Figure 1:
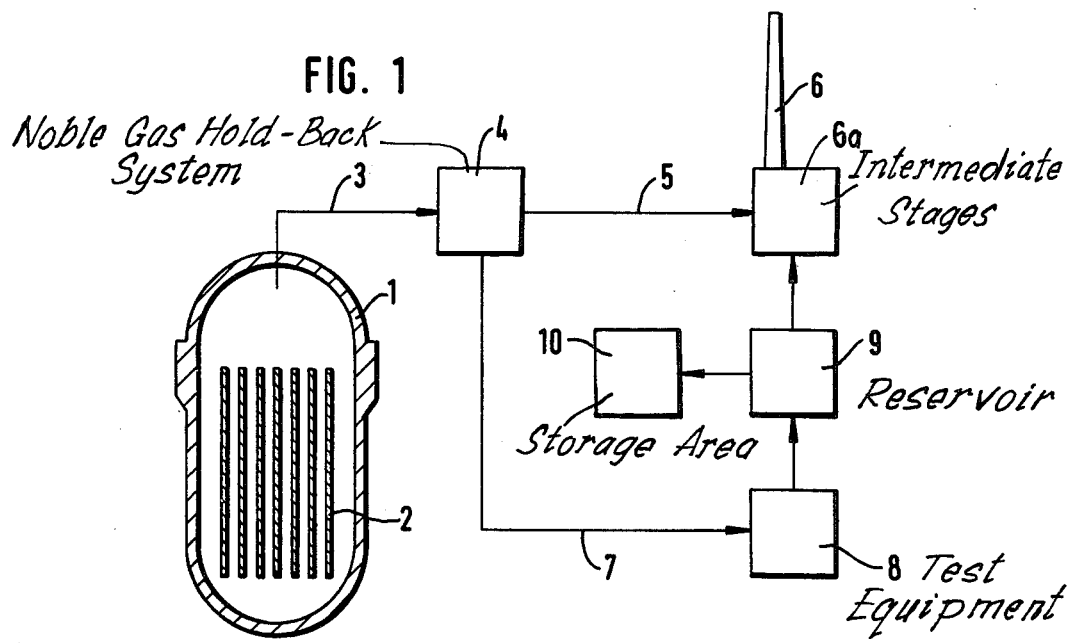

United States Patent [19]

Michaelis et al.

[11] 4,204,908
[45] May 27, 1980

[54] METHOD OF IDENTIFYING LEAKY COMPONENTS OF A MULTI-COMPONENT SYSTEM

[75] Inventors: Walfried Michaelis, Bullenhausen; Claus Weitkamp, Wentorf, both of Fed. Rep. of Germany

[73] Assignee: Gesellschaft für Kernenergieverwertung in Schiffbau und Schiffahrt mbH, Geesthacht-Tesperhude, Fed. Rep. of Germany

[21] Appl. No.: 868,796

[22] Filed: Jan. 12, 1978

[30] Foreign Application Priority Data

Jan. 12, 1977 [DE] Fed. Rep. of Germany ....... 2700952

[51] Int. Cl.² .............................................. G21C 17/00
[52] U.S. Cl. .................................................. 176/19 LD
[58] Field of Search ................... 176/19 LD; 250/343; 356/326, 328

[56] References Cited

U.S. PATENT DOCUMENTS

| | | | |
|---|---|---|---|
| 3,820,901 | 6/1974 | Kreuzer | 356/326 |
| 3,851,176 | 11/1974 | Jeunehomm et al. | 250/343 |
| 3,861,809 | 1/1975 | Hall, Jr. | 250/343 |
| 3,864,613 | 3/1975 | Link et al. | 250/343 |
| 3,911,276 | 10/1975 | Bell | 250/343 |
| 3,956,069 | 5/1976 | McCormick | 176/19 LD |
| 3,995,960 | 12/1976 | Fletcher et al. | 250/343 |
| 4,051,372 | 9/1977 | Aine | 356/51 |

OTHER PUBLICATIONS

Nuclear Technology, vol. 26 (8/75) pp. 472–479, Strand et al.
Nuclear Technology, vol. 29 (5/76) pp. 200–208, Mc-Cormick et al.

*Primary Examiner*—Samuel W. Engle
*Assistant Examiner*—S. A. Cangialosi
*Attorney, Agent, or Firm*—Becker & Becker, Inc.

[57] ABSTRACT

A method of identifying leaky components of a multi-component system in which the individual components contain a charge. Additional substances having different element or isotope compositions are added to these charges to code them. If leaks occur, element or isotope analysis of the escaping charges then allows identification of the leaky component. If the multi-component system includes a nuclear reactor, different element or isotope combinations of krypton and xenon may be added to the individual fuel rods during production, and optical saturation spectroscopy may be used to analyze the leaking gases.

1 Claim, 2 Drawing Figures

METHOD OF IDENTIFYING LEAKY COMPONENTS OF A MULTI-COMPONENT SYSTEM

Many commercial systems are composed of a fairly large number of identical or similar components on which specific requriements are imposed with regard to soundness or tightness. For safe or economic operation of such systems, it is necessary or advantageous to identify leaky components rapidly and, if possible, even without interrupting operation. The present invention relates to a method which permits such identification.

A typical multi-component system is the nuclear reactor. The core of the reactor is composed of a large number of fuel elements consisting in turn of a greater number of fuel rods. The fuel rods and elements are subjected to radiological, chemical, thermal and mechanical stresses which may result in leaks. Consequently, fission products and, under certain conditions, also fuel may pass into the coolant, from which they can be removed only at considerable expense. In order to ensure that there is as little radiological contamination of the environment as possible, leaky components may be removed if necessary from the core.

The problem has been solved heretofore by monitoring the radioactivity of the coolant and of the volume of gas above it. This method, however, only permits a conclusion that fuel elements are leaky, but in no way at all does it allow a determination of from which fuel elements fission products have escaped. The practice followed heretofore therefore results in the reactor possibly having to be shut down for a lengthy period of time if too many fuel elements are leaky. A leakage check on the individual fuel elements by visual inspection or by the conventional method of non-destructive testing is not possible at all inside the reactor, and is possible outside the reactor only under conditions of considerable complexity.

Knowledge of leaky fuel elements is also of importance for their reprocessing, and in particular for the storage and transport of the burned-away elements, because leaky fuel elements which release radioactivity require special treatment. For planning and calculation, it is generally assumed that about 1% of the individual rods become defective in operation. In practice, however, considerably higher rates of defectiveness have also occurred.

It is an object of the present invention to allow identification of individual leaky elements or rods.

Figure 2:
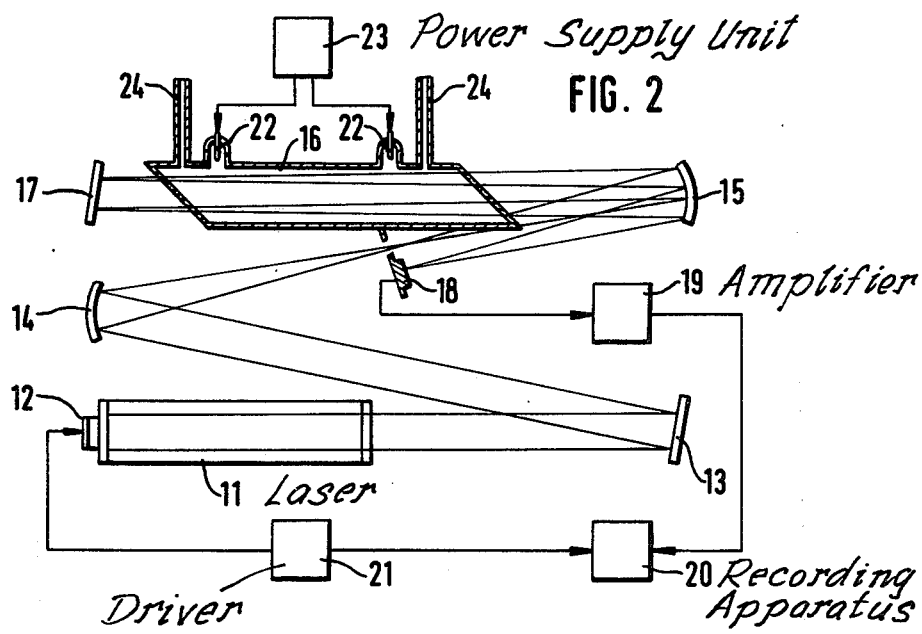

This object and other objects and advantages of the present invention will appear more clearly from the following specification in connection with the accompanying drawing, in which:

FIG. 1 is a schematic representation of an apparatus for carrying out the method of the present invention, using a nuclear reactor as an example; and FIG. 2 shows one possibility of isotope analysis using saturation spectroscopy.

The present invention is based on the fact that in some commercial systems the components contain a charge of gases or other substances. According to the present invention, the identification of individual leaky components is characterized primarily in that additional substances having different element and/or isotope compositions are added to the charges of the respective components during production or specifically during operation, and those portions of the charge which escape in the event of leaks are collected and are subjected to element and/or isotope analysis of the additional substances, if necessary after chemical or physical separation of these substances. This method will be described in detail using as an example the multicomponent system of a nuclear reactor.

In the production of fuel rods for nuclear reactors, before the individual rods are fused or welded, the space (the so-called plenum) left free from fuel pellets at the ends of each rod, and the gaps between the fuel and the wall and between the individual fuel pellets, are supplied with a charge of noble gas, the pressure of which is in the range of 20 to 50 atmospheres or even higher, depending on the type of reactor. This charge of noble gas fulfills a threefold purpose; namely, first, it permits testing of the weld for leaks, second, it offers a pressurizing or initial stress for partially compensating the pressure of the coolant or cooling fluid acting on the rod from outside, and third, it improves the transfer of heat in the interior of the rod, as long as the fuel pellets do not rest against the wall.

According to a preferred embodiment of the present invention, in place of the pure helium heretofore used as the noble gas charge, a noble gas consisting of a plurality of stable isotopes is used, this noble gas being pure or admixed with helium. For this purpose, the noble gases krypton and xenon may be used and, according to the invention, are added to the various fuel elements or rods in different isotopic compositions, i.e. each individual element or each rod is coded by the composition of the gas which is put in. If a fuel element or a fuel rod develops a leak, charging gas escapes; with a suitable choice of the compositions of the charges, isotope analysis of the volume of gas above the cooling fluid permits identification and location of the defective element or rod.

The noble gases krypton and xenon occur in natural air only in proportions of 1.14 ppm and 87 ppb, respectively. They consist of six and nine stable isotopes, respectively; moreover, there is a fairly large number of radioactive isotopes of both gases. In choosing the composition of the charging gas, attention must be paid to the fact that during the nuclear fission, in addition to radioactive isotopes, stable krypton and xenon isotopes are also produced in the fuel elements of a reactor, and these could falsify the result. The proportions, it is true, are not high; on the basis of realistic assumptions, and presuming that the gas charge consists of pure krypton or xenon, they are about 0.1% (Kr) or 1% (Xe) of the charge at the end of the life of a fuel element, and are correspondingly lower in the event of the element or rod leaking at an earlier point in time. If only a few fuel rods develop leaks, this so-called stable fission noble gas does not substantially impair the reliability of the method of the invention. For larger quantities of leaky elements, the problem of interference by stable fission noble gas can be obviated as follows:

In the case of krypton, only the three heaviest isotopes (out of a total of six), and in the case of xenon, only the four heaviest isotopes (out of a total of nine), occur as fission products. The referenced interference effects between the charging gas and stable fission noble gas are therefore completely eliminated if one uses only the three lightest isotopes (Kr) or five lightest isotopes (Xe) in the charging or analysis.

When applying the invention to nuclear reactors, it is useful, for determining the isotopic composition of the escaping noble gases, if, in order to separate radioactive fission noble gases in power plant reactors, noble gas hold-back systems, which permit krypton and xenon to be separated, are planned or are already in operation.

Naturally, with these systems, the stable isotopes of the two noble gases are also retained, so that they are available in more concentrated form for testing. Although modern methods of isotope analysis are very sensitive, in most cases testing the concentrated gas improves sensitivity and accuracy, and a simpler test apparatus can be employed.

Two principles are available for the testing itself, one of which is based on the different masses (so-called mass spectrometry), and the other on the small differences in the wavelengths of the optical spectral lines of the various isotopes (optical spectrometry).

Of the various structural forms of apparatus for mass spectrometry, the so-called quadrupole mass filter is very suitable for the method of the invention. The quadrupole mass filter is at the same time the simplest and cheapest mass spectrometer.

An inherent characteristic of mass spectrometry is the fact that the substance to be analyzed is consumed. If only very small amounts of substance are available, optical methods therefore offer advantages, since a single atom or molecule can be brought to absorption and/or emission as many times as desired in certain circumstances. Because of the possibility of complete enclosure of the test substance, optical methods moreover facilitate the handling of mixtures of stable and radioactive substances.

Difficulty is caused in optical isotope analysis by the fact that the differences in the wavelengths of the spectral lines of the individual isotopes (so-called isotopic shifts) of a krypton or xenon mixture are so small that they lie within the normal width, as usually observed, of the spectral lines.

This width is caused by two phenomena, namely, first, by the collisions of the individual gas particles (atoms) with one another (so-called pressure broadening), and second, by the rapid disordered movement of the gas atoms (so-called Doppler broadening). A feature of the present invention is also the application of artifices known per se to the determination of isotopic conditions, thus permitting the elimination of these two effects and observance of the optical isotopic shift.

Basically, the following possibilities, among others, are available for this purpose:

1. Reduction of the frequency of collision of the gas atoms by reduction of the pressure and velocity by lowering the temperature.
2. Reduction of the frequency of collision and conversion of the disordered velocity into an orderly velocity by generating a gas stream flowing out into a vacuum, the gas stream being observed perpendicular to the direction of flow (so-called atomic beam method).
3. Reduction of the pressure and excitation of the atoms with two light quanta, each of which contains only half the necessary energy, but which come from opposite directions, so that their Doppler shifts of equal amount in opposite directions exactly compensate each other (so-called two-photon spectroscopy).
4. Reduction of the pressure and reflection of the light beam into itself. If the wavelength of the light beam is different from the wavelength of the line center, the beam "sees", both on the way out and on the way back, atoms whose direction and speed of flight are of such a nature that they are able to absorb the light; in the line center, however, the atoms which are capable of absorption on the way back have already absorbed on the way out and are therefore eliminated for further absorption and, with suitable choice of the physical conditions, the total absorption drops again in the line center: the wide absorption line shows a narrow indentation, the so-called Lamb Dip, in its center (Lamb Dip or saturation spectroscopy).

Referring now to the drawing in detail, the arrangement shown in FIG. 1 comprises a reactor having a pressure vessel 1 and fuel elements 2. The used air 3 from the reactor passes into a noble gas hold-back or retaining system 4. The used air 5, free from krypton or xenon, is delivered to the chimney 6 by way of intermediate stages 6a which are not important here, and the noble krypton or xenon gases 7 pass into the test equipment 8 for determining the composition of the noble gas. After the testing, the noble gases are either delivered to the chimney 6 via a reservoir 9, or are conveyed to a storage area 10.

In FIG. 2, the light of variable wavelength of a laser 11, the frequency of which can be varied by means of an end mirror 12 mounted on a piezoelectric quartz crystal, passes by way of optical elements (mirrors 13, 14, 15) through a photo-tube or cell 16 containing the sample gas, onto a mirror 17, which reflects it back into itself, so that it again passes through the cell 16 and strikes the mirror 15. If, for example, the mirrors 14 and 15 are formed as concave mirrors of suitable curvature, and the end mirror 17 is tilted slightly out of the normal to the incident beam, the focal points or foci between the mirrors 14 and 15 for the incident and returning beams are not located in exactly the same place. Mounting a detector 18 at the focus of the reflected beam allows the intensity of the reflected signal to be recorded, and the wavelength-dependence of the absorption by the sample gas in the cell to be determined, if the detector signal is suitably conditioned in an amplifier 19 and is registered by a recording apparatus 20 (oscilloscope, recorder or the like) as a function of the wavelength, for which, among others, the voltage from the driver 21 of the piezoelectric quartz crystal is a measure.

It is true that at the present time no lasers having suitable characteristics (wavelength, intensity, variable-frequency range) are known for direct excitation of the noble gases xenon and krypton out of their original atomic state. The gas must therefore be pre-excited, which can, for example, be done electrically with the aid of electrodes 22 fused into the cell and served by a power supply unit 23. If the cell is provided with gas inlet and outlet connections 24, quasi-continuous operation is also possible by passing the gas through the cell.

It is, of course, to be understood that the present invention is in no way limited to the specific disclosure of the drawing, but also encompasses any modifications within the scope of the appended claims.

What we claim is:

1. A method of identifying leaky components of a multi-component nuclear reactor system in which the components contain a nuclear fuel charge, which includes in combination the steps of:

adding additional substances which are noble gases having different compositions, including different element and isotope compositions, to the charges of the respective components;

collecting from the used air of the nuclear reactor those portions of the nuclear fuel charges which escape in the event of leaks;

subjecting said collected portions to appropriate element and isotope analysis of said additional substances, prior to the analysis, separating the additional substances chemically and/or physically from the portions of the charge escaping in the event of leaks, optically determining the composition of the additional substances, the isotope composition of the additional substances being determined by optical saturation spectroscopy, determining the absorption of radiation from a variable-frequency laser in a cell filled with the sample substance as a function of the wave-length, and eliminating the collision and Doppler broadening by measuring the Lamb Dip at reduced pressure.

* * * * *